US006796998B2

(12) United States Patent
Schaldach et al.

(10) Patent No.: US 6,796,998 B2
(45) Date of Patent: Sep. 28, 2004

(54) STENT

(75) Inventors: Max Schaldach, deceased, late of Erlangen (DE); by Max Schaldach, Jr. legal representative, Berlin (DE); Daniel Lootz, Warnemuende (DE); Karsten Koop, Rostock (DE); Curt Kranz, Berlin (DE)

(73) Assignee: Biotronik Mess- und Therapiegeraete GmbH & Co. Ingenieurbuero, Berlin (DE)

( * ) Notice: Subject to any disclaimer, the term of this patent is extended or adjusted under 35 U.S.C. 154(b) by 373 days.

(21) Appl. No.: 09/974,770

(22) Filed: Oct. 9, 2001

(65) Prior Publication Data

US 2002/0049494 A1 Apr. 25, 2002

(30) Foreign Application Priority Data

Oct. 10, 2000 (DE) .......................................... 100 50 940

(51) Int. Cl.[7] ................................................. A61F 2/06
(52) U.S. Cl. ..................................................... 623/1.15
(58) Field of Search ................................ 623/1.15, 1.1, 623/1.16–1.22, 23.7; 606/200

(56) References Cited

U.S. PATENT DOCUMENTS

| | | | | |
|---|---|---|---|---|
| 5,716,393 A | * | 2/1998 | Lindenberg et al. | 623/1.2 |
| 6,042,606 A | * | 3/2000 | Frantzen | 623/1.18 |
| 6,068,656 A | | 5/2000 | von Oepen | |
| 6,488,702 B1 | * | 12/2002 | Besselink | 623/1.15 |

FOREIGN PATENT DOCUMENTS

| | | |
|---|---|---|
| DE | 297 08 879 U1 | 9/1997 |
| DE | 198 22 157 A1 | 11/1999 |
| EP | 1 029 517 A2 | 8/2000 |

OTHER PUBLICATIONS

Serruys, Patrick W. and Michael JB Kutryk, "Handbook of Coronary Stents", Martin Dunitz (London, England), p. 111–19, (Oct. 4, 1998).

* cited by examiner

*Primary Examiner*—(Jackie)Tan-Uyen T. Ho
(74) *Attorney, Agent, or Firm*—Hahn Loeser & Parks LLP

(57) ABSTRACT

A stent, in particular a coronary stent, for expansion from a first condition into an expanded second condition in which it holds a vessel in an expanded state, comprising a tubular body whose peripheral surface (1) is formed by a number of annular support portions (2, 2.1, 2.2, 2.3) comprising bar elements (3, 3.1, 3.2, 3.3) which are connected in the longitudinal direction of the stent by way of connecting bars (4, 4.1, 4.2), wherein the bar elements (3.1) of at least a first support portion (2.1) and a second support portion (2.2) in adjacent relationship in a first direction (6.1) extend in a meander configuration in the peripheral direction of the stent and the connecting bars (4, 4.1, 4.2) to the second support portion (2.2) engage in the region of the turning points (5, 5.2, 5.3) of the first support portion (2.1), which turning points face in the first direction (6.1), wherein at least two adjacent connecting bars (4.1, 4.2) engage respectively in the region of a turning point (5.1) of the second support portion (2.2), which turning point projects in a second direction (6.2) in opposite relationship to the first direction (6.1).

42 Claims, 3 Drawing Sheets

STENT

The invention concerns a stent, in particular a coronary stent, for expansion from a first condition into an expanded second condition in which it holds a vessel in an expanded condition, comprising a tubular body whose peripheral surface is formed by a number of annular support portions comprising bar elements which are connected in the longitudinal direction of the stent by way of connecting bars. The bar elements of at least a first support portion and a second support portion in adjacent relationship in a first direction extend in that case in a meander configuration in the peripheral direction of the stent and the connecting bars to the second support portion engage in the region of the turning points of the first support portion, which turning points face in the first direction.

BACKGROUND OF THE ART

A stent is what is known as an intraluminal expansion element which is used to hold a vessel, for example a blood vessel, in the human or animal body, in an expanded state. For that purpose the stent in a compressed first condition is moved by means of a suitable catheter to the location in the vessel, which is to be held in the expanded state. When the implantation location is reached the stent is radially expanded into an enlarged second condition. In the case of what is known as balloon-expansible stents the stent is expanded by means of a balloon catheter to such a great degree that, by virtue of plastic deformation, it maintains its expanded second condition even after removal of the balloon, and thus supports the vessel. In the case of what are referred to as self-expanding stents, the stent is held in a compressed first condition against a return force, for example by a sheathing catheter. That constraint is released at the implantation location so that the stent of its own accord assumes an expanded second condition.

Thus for example there is the known NIR-stentTM from Medinol Ltd., Tel Aviv, Ill., in which reversal or turning points which are respectively aligned with each other in the longitudinal direction of the stent, of two bar elements extending in a meander configuration, are-connected by way of an arcuate connecting bar. Known stents of that kind on the one hand frequently involve the problem that their position in the vessel once they have been placed and expanded, can only be corrected with difficulty, as a result of the biasing effect between the vessel and the stent. On the other hand, the problem which often already arises when moving the stent to the implantation location is that regions of the bar elements or the connecting bars, which project in the distal direction, that is to say in the direction of insertion, hookingly engage the wall of the vessel precisely in curved regions thereof, and are bent radially outwardly, which is frequently also referred to as "fishscaling".

SUMMARY OF THE INVENTION

Therefore the object of the present invention is to provide a stent of the kind set forth in the opening part of this specification, which does not suffer from the above-indicated disadvantages or which suffers therefrom only to a lesser degree, and which in particular permits an easier variation in its position with respect to the vessel after expansion thereof.

Based on a stent as set forth in the classifying portion of claim 1, that object is attained by the features recited in the characterizing portion of claim 1.

The present invention is based on the technical teaching that a more easily repositional stent is obtained if at least two respective adjacent connecting bars engage in the region of a reversal or turning point of the second support portion, which turning point projects in a second direction in opposite relationship to the first direction. By virtue of the connecting bars being brought together in the region of a turning point of the bar element of the second support portion, when a tensile force is applied to the stent in the first direction, force components which are directed towards each other are exerted in the peripheral direction on the engagement points in question of the connecting bars on the bar element of the first support portion. They are thereby moved towards each other, whereby the diameter of the stent is reduced and thus the stent can be more easily displaced with respect to the vessel in the first direction.

In that arrangement the connecting bars do not necessarily have to be brought together at the turning point. They may also engage at a certain spacing from the turning point of the bar element of the second support portion.

In the same advantageous manner it is possible to use the stent according to the invention in conjunction with a sheathing catheter of correspondingly small outside diameter, into which the stent can be drawn by applying a suitable pulling force in the first direction for repositioning purposes, that is to say for correcting its position in the vessel, or which can be pushed over the stent for repositioning purposes.

Two and more adjacent connecting bars can engage the region of the turning point which projects in the second direction. Preferably however precisely two adjacent connecting bars engage the region of the turning point which projects in the second direction, as in that case then there is no further connecting bar to impede the movement towards each other of the two engagement points on the first support portion, thereby to produce a particularly effective reduction in diameter.

The bar elements of the first and second support portions can be arranged in any desired manner with respect to the peripheral direction of the stent. Preferably the bar elements of the first and second support portions extend substantially in phase with each other with respect to the peripheral direction of the stent, whereby a symmetrical configuration of the connecting bars with respect to the longitudinal direction of the stent and thus an advantageous uniform application of force to the bar elements is possible.

The connecting bars can be brought together at various turning points of the second support portion. Thus for example in the case of bar elements which are in phase with each other in the peripheral direction, it is possible for the connecting bars to be brought together respectively in the region of turning points, which are aligned with each other in the longitudinal direction of the stent, of the bar elements.

In preferred variants of the stent according to the invention the first support portion has first and second turning points which are in adjacent relationship in the peripheral direction of the stent and which project in the first direction and the region of which is engaged by connecting bars to different turning points of the second support portion. Arranged between those turning points is a third turning point which projects in the second direction and the region of which is engaged by the two connecting bars of a support portion in adjacent relationship in the second direction with the first support portion, with bar elements extending in a meander configuration in the peripheral direction of the stent. That arrangement affords particularly good distribution of the support locations for the vessel.

In further preferred embodiments of the stent according to the invention the bar elements and additionally or alternatively the connecting bars are adapted to increase the flexibility of the stent. That can be effected in many known ways.

Preferably for that purpose at least one support portion is formed by a bar element whose direction of curvature changes in the central region between two turning points. Additionally or alternatively at least the connecting bars between the first and second support portions are of a curved configuration, wherein their direction of curvature changes in the central region between the two points of engagement on the support portions. The respective S-shaped configuration reduces the stiffness of the elements in question, in the longitudinal direction of the stent, and thus enhances flexibility of the stent, with respect to its longitudinal axis. The stent can thus more easily follow curved vessel configurations.

Advantageous variants of the stent according to the invention are distinguished in that the bar elements and additionally or alternatively the connecting bars are adapted to achieve a stress distribution which is as uniform as possible upon deformation, in particular upon expansion of the stent. This also can be effected in many known ways.

Preferably for that purpose at least one support portion is formed by a bar element whose width decreases towards the center between two turning points. Additionally or alternatively the width of at least the connecting bars between the first and second support portions decreases towards the center between the two engagement points on the support portions.

In embodiments which are advantageous because they are simple to manufacture because of the simple geometry involved, at least one support portion is formed by a bar element which extends in a meander configuration in the peripheral direction of the stent, wherein each two bar element portions which are in adjacent relationship in the peripheral direction of the stent and which extend between the turning points form the limbs of a V-shape.

Further preferred variants of the stent according to the invention are distinguished in that the geometry of the bar portions and additionally or alternatively of the connecting bars is so selected that the stresses which occur therein upon expansion of the stent are above the elastic deformation limit and below the rupture limit of the stent material. Additionally or alternatively the width of the bar elements and additionally or alternatively of the connecting bars may vary over the length thereof in such a way that the stresses which occur therein upon expansion of the stent are above the elastic deformation limit and below the rupture limit of the stent material. That ensures that upon expansion the stent is advantageously substantially uniformly plastically deformed.

BRIEF DESCRIPTION OF THE DRAWINGS

Further preferred embodiments of the present invention are set forth in the appendant claims and the description hereinafter of preferred variants of the stent according to the invention with reference to the accompanying drawings in which:

DETAILED DESCRIPTION OF THE INVENTION

Figure 1:
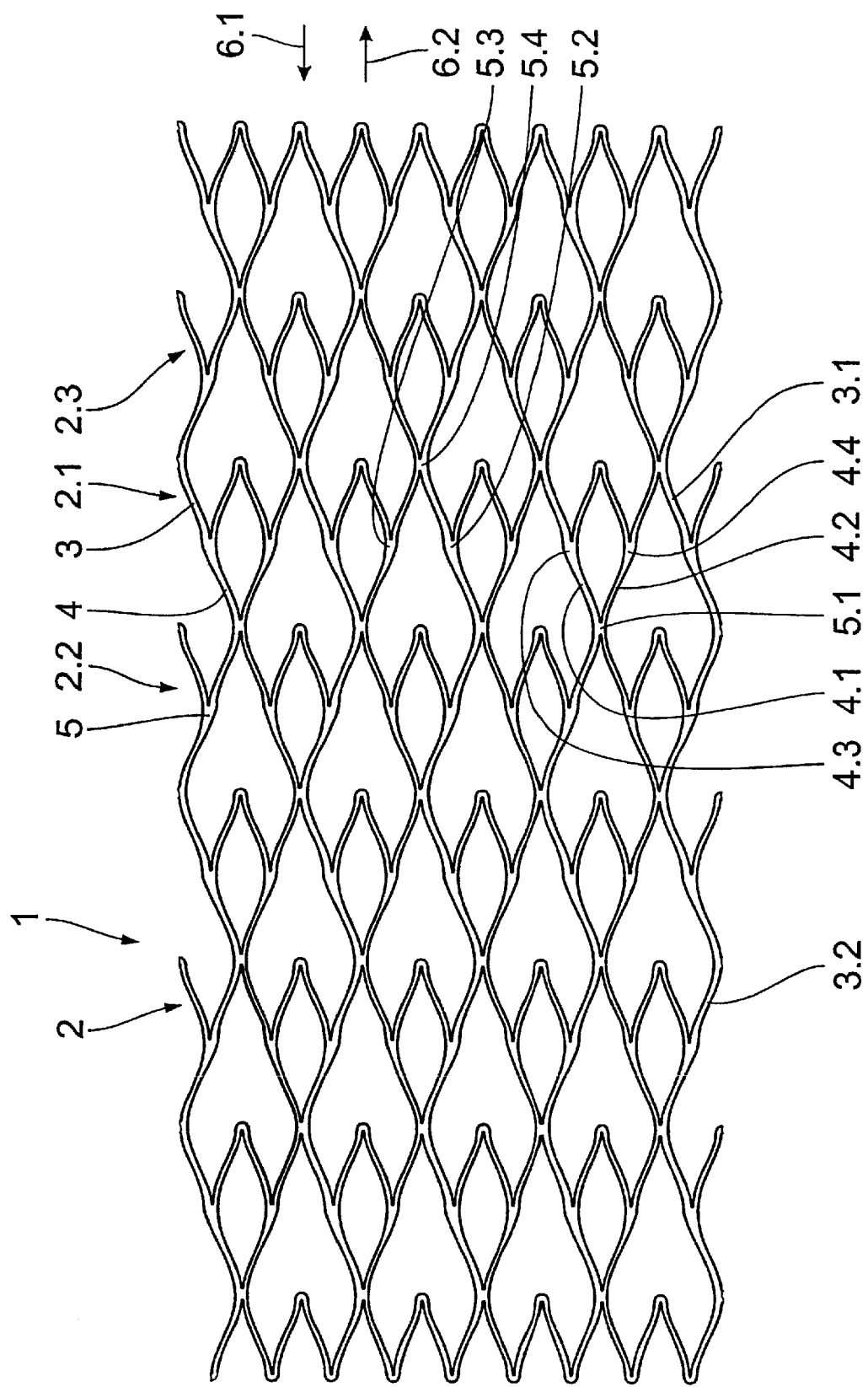
FIG. 1 is a view onto the development of the peripheral surface of a preferred embodiment of the stent according to the invention.

FIG. 1 is a view onto the development of the peripheral surface 1 of a preferred embodiment of a stent according to the invention having a number of annular support portions 2. The development of the peripheral surface 1 is shown in the first condition of the stent in which it can be inserted into the blood vessel. In the illustrated example the stent consists exclusively of support portions 2 formed by bar elements 3 which extend in a meander configuration in the peripheral direction of the stent. The bar elements 3 are connected together in the longitudinal direction of the stent by way of connecting bars 4.

In this arrangement the connecting bars 4 respectively engage in the region of turning or reversal points 5 of the bar elements 3. In the illustrated example the stent consists exclusively of first support portions 2.1 and second support portions 2.2 in adjacent relationship therewith in a first direction 6.1. The connecting bars are so arranged that each two adjacent connecting bars 4.1 and 4.2 engage in the region of a turning point 5.1 of the second support portion 2.2, which turning point projects in a second longitudinal direction 6.2. The second longitudinal direction 6.2 is in this case in opposite relationship to the first longitudinal direction 6.1.

In the illustrated example each turning point 5 of the first support portion 2.1, which turning point projects in the first direction 6.1, is engaged by a respective connecting bar 4. The connecting bars are brought together in pairs in the described fashion at a turning point 5.1 of the second support portion 2.2, which turning point projects in the second longitudinal direction 6.2. In this case the bar elements 3.1 and 3.2 forming the respective support portions 2.1 and 2.2 respectively are of a periodic configuration, extending in phase with each other with respect to the peripheral direction of the stent so that the connecting bars 4.1 and 4.2 connect in a V-shape to the turning point 5.1.

In the illustrated example, the configuration selected is such that the first bar element 3.1 and therewith the first support portion 2.1 have first and second turning points 5.2 and 5.3 which are in mutually adjacent relationship and in the region of which engages a respective connecting bar to a different turning point 5 of the second support portion 2.2 which is in adjacent relationship in the first direction 6.1. Disposed between those turning points 5.2 and 5.3 is a third turning point 5.4 which projects in the second direction 6.2. Once again, the region of that third turning point 5.4 is engaged by two connecting bars to a support portion 2.3 which is in adjacent relationship in the second longitudinal direction 6.2. That configuration affords particularly good distribution of the support locations for the blood vessel which is to be supported.

The bar elements 3 are designed to increase the flexibility of the stent, insofar as their direction of curvature changes in the central region between two turning points 5. The same applies in regard to the connecting bars 4 which are of a curved configuration in order to increase flexibility, wherein their direction of curvature changes in the central region between the two engagement points on the support portions. That slightly S-shaped configuration affords a lower degree of stiffness of the bar elements in relation to forces acting in the longitudinal direction of the stent and thus provides enhanced stent flexibility.

The bar elements 3 and the connecting bars 4 are also designed to achieve stress distribution which is as uniform as possible, upon deformation of the stent. An advantageous stress distribution is achieved on the one hand by the width of the bar elements 3 continuously decreasing towards the center between two turning points 5, although this is not shown in FIG. 1. In the described example the decrease in thickness is about 50%. In other embodiments of the bar element however it is determined in dependence on the rest of the geometry of the bar element, in accordance with the respective upper stress limit to be observed.

A further advantageous influence on stress distribution within the bar element 3 is afforded by the change in the direction of curvature of the bar element 3 in the central region between two turning points 5. Therefore, each two bar element portions which are in adjacent relationship in the peripheral direction of the stent and which extend between the turning points 5 form the curved limbs of a V-shape.

An additional influence on the stress distribution over the bar element 3, which is advantageous in the above-indicated sense, is afforded by the bar element 3 being in the shape of a segment of an elliptical arc in the region of the turning points 5, instead of the usual segment of a circular arc.

The described widthwise variation and the curvature configuration are embodied in the connecting bars 4, with the described advantages in terms of stress distribution, in the same manner—this is also not shown in FIG. 1.

The described widthwise variation and the curvature configuration of the bar elements 3 and the connecting bars 4 also provide that the stresses which occur therein upon expansion of the stent are above the elastic deformation limit and below the rupture limit of the stent material.

If a pulling force is applied to the stent in the first direction 6.1 when the stent is being moved to the implantation location or for example when changing the position of the stent when already implanted, then the connecting bars 4.1 and 4.2 which are brought together to the turning points 5.1 produce forces on the bar element 3.1, which move the engagement points 4.3 and 4.4 of the connecting bars 4.1 and 4.2 towards each other. That causes the bar element 3.1 in question to be drawn together in the peripheral direction of the stent, thereby resulting in a reduced diameter and thus easier displacement of the stent with respect to the blood vessel into which it is inserted.

This effect moreover can also be used, for example for the purposes of changing the position of the expanded stent with respect to the blood vessel, for pulling the expanded stent into a sheathing catheter of correspondingly small outside diameter in the first direction 6.1 and thus for example putting it into its first condition again. That can be used in a particularly advantageous fashion, in conjunction with what is referred to as a self-expanding stent. In this respect moreover it is advantageous that the stent does not have any portions which project in the first direction 6.1 and which upon movement of the stent in the first direction 6.1 could come into hooking engagement on the blood vessel or such a sheathing catheter. Accordingly, a "fishscaling" effect cannot occur upon movement of the stent in the first direction 6.1.

Figure 2:
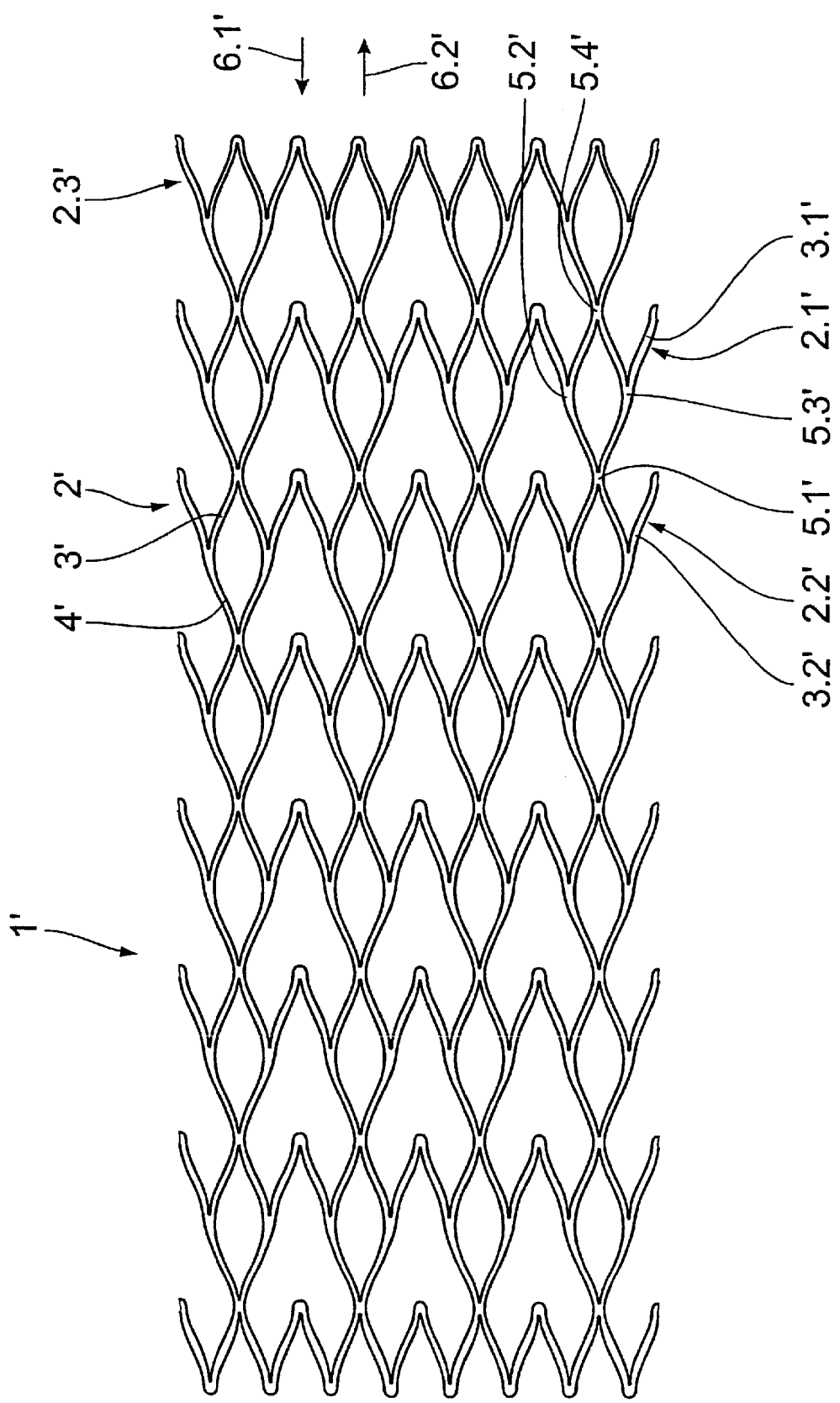
FIG. 2 is a view onto the development of the peripheral surface of a further preferred embodiment of the stent according to the invention.

FIG. 2 is a view onto the development of the peripheral surface 1' of a preferred embodiment of a stent according to the invention having a number of annular support portions 2'. The development of the peripheral surface 1' is shown in the first condition of the stent in which it can be introduced into the blood vessel. In the illustrated example the stent consists exclusively of support portions 2' which are formed by bar elements 3' extending in a meander configuration in the peripheral direction of the stent. The bar elements 3' are connected together in the longitudinal direction of the stent by way of connecting bars 4'.

The embodiment of FIG. 2 is the same in terms of its fundamental structure and its fundamental function as the variant shown in FIG. 1 so that here only the differences will be discussed, which in this case lie in the arrangement of the connecting bars 4 over the stent.

The difference is that the adjacent bar element 3.1' and therewith the first support portion 2.1' has mutually adjacent first and second turning points 5.2' and 5.3', the regions of which are engaged by the respective connecting bars to the turning point 5.1 of the second support portion 2.2' which is in adjacent relationship in the first direction 6.1'. Arranged between those turning points 5.2' and 5.3' is a third turning point 5.4' projecting in the second direction 6.2'. The region of that third turning point 5.4' is in turn engaged by two connecting bars to a support portion 2.3' in adjacent relationship in the second longitudinal direction 6.2'. That configuration affords further particularly good distribution of the support locations for the blood vessel which is to be supported.

In the examples shown in FIGS. 1 and 2 the stents each exclusively consist of bar elements which extend in a meander configuration in the peripheral direction of the stent and which are of the described configuration and arrangement. It will be appreciated however that the stent may also comprise in portion-wise manner in the longitudinal direction, support portions which are designed in a different fashion and which in particular include bar elements of a different configuration.

Figure 3:
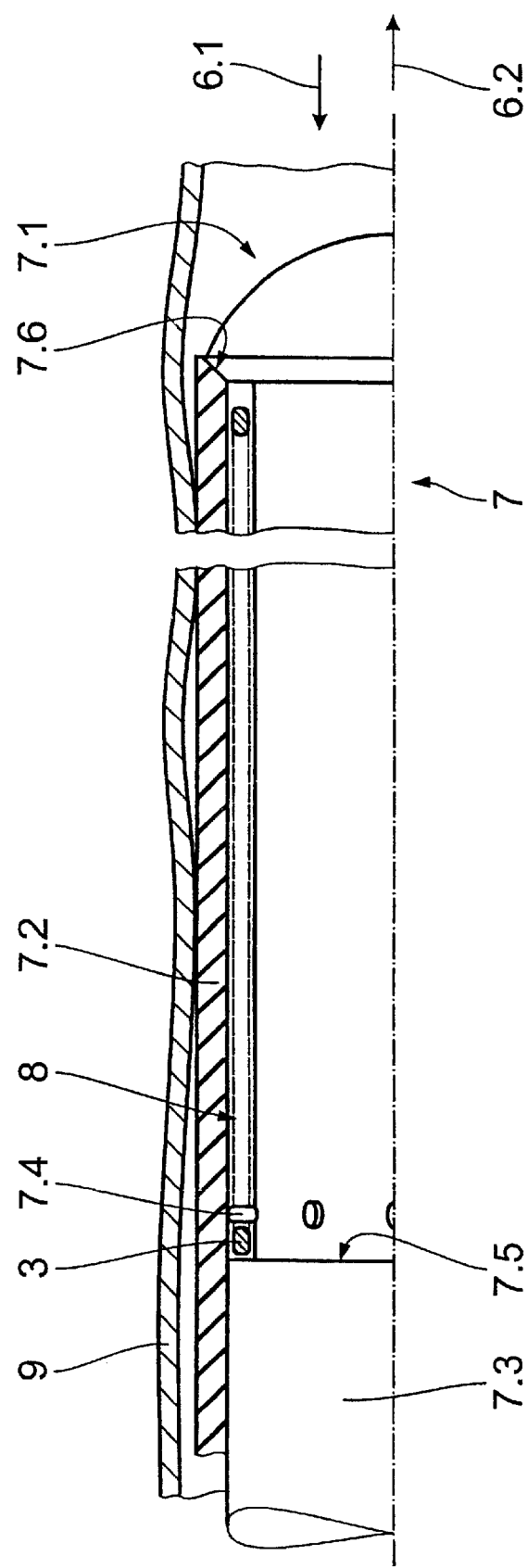
FIG. 3 is a diagrammatic section through a stent according to the invention arranged on a catheter.

FIG. 3 is a diagrammatic section through a catheter 7 for implanting a stent 8 according to the invention as shown in FIG. 1, comprising a distal end 7.1, in the region of which there is provided a sheathing device in the form of a sheathing tube 7.2 for receiving the stent 8 in its first condition—as shown in FIG. 3. The catheter 7 is introduced into a blood vessel 9 in that state.

The catheter 7 has a device 7.3 arranged displaceably with respect to the sheathing device 7.2, for producing a relative movement between the sheathing device 7.2 and the stent 8 in the first longitudinal direction 6.1. The device 7.3 has a holding device in the form of projections 7.4 which engage behind the bar elements so that a pulling force can be applied to the stent 8 in the first longitudinal direction 6.1. The device 7.3 further includes a step 7.5 by way of which a pressure force can be applied to the stent 8 in the second longitudinal direction 6.2 in order to push the stent 8 out of the sheathing device 7.2 again.

In that way it is easily possible for the stent 8 which is held by the holding device 7.4 to be restored to its first condition. That can be effected for example by a procedure whereby, with the sheathing device 7.2 being held fast, the stent is retracted into the sheathing device 7.2 by displacement of the holding device 7.4 with respect to the sheathing device 7.2, in which case the stent is then constrained to a reduced diameter from its expanded diameter by the leading edge 7.6. It will be appreciated that alternatively the stent 8 can also be held in position by way of the holding device 7.4 and the sheathing device 7.2 can be pushed over the stent 8 by means of a suitable device.

These catheters 7 can be used both with self-expanding and also with balloon-expansible stents. Preferably such a catheter is already provided with a stent according to the invention, which is arranged in the sheathing device 7.2 of the catheter.

In that respect for positioning a stent 8 in a vessel 9 the procedure adopted can be that set out below. This may involve both positioning the stent in vivo and also in vitro, for example for test purposes. Thus for example the self-expanding stent 8 which is disposed in a sheathing device is moved in a first step to the expansion location with the stent 8 in its first condition. Then in a second step the stent 8 is at least partially expanded by at least partial removal of the sheathing device 7.2 from the stent 8. In a checking step, the position of the stent 8 with respect to the expansion location is detected. It can be provided in that respect that the stent 8 is only partially expanded in the second step. In at least one correction step, the stent 8 is then put into its first condition again, in which it is then disposed in the sheathing device 7.2, and then the position of the stent is altered with respect to the expansion location. That correction step can also be repeated a plurality of times before the stent is then definitively completely expanded.

The same method principle can also be implemented with a balloon-expansible stent which firstly is moved possibly at least over a part of its length without sheathing device to the implantation location and then repositioned in the above-described manner, using a sheathing device. In that case in the correction step the stent is put into a third condition in which it is arranged in the sheathing device. That third condition can correspond to the first condition. In that respect however, in comparison with its first condition, the stent can also be in a preferably partially expanded condition, but also a still further compressed condition.

What is claimed is:

1. A stent for expansion from a first condition into an expanded second condition in which it holds a vessel in an expanded state, comprising:
   a tubular body having a peripheral surface that is formed by a plurality of annular support portions that each comprise:
   a plurality of bar elements; and
   a plurality of connecting bars that connect the bar elements in a longitudinal direction of the stent;
   wherein the bar elements or at least a first annular support portion and a second annular support portion in adjacent relationship in a first direction extend in a meander configuration in a peripheral direction of the stent,
   wherein each of the connecting bars projecting from the second annular support portion connects to a turning point of the first annular support portion, which faces in the first direction,
   such that at least two connecting bars in adjacent relationship respectively and projecting from two different turning points of the first annular support portion connect to the second annular support portion at a turning point which faces in a second direction in opposite relationship to the first direction, and
   such that the first annular support portion has first and second turning points that are in adjacent relationship in the peripheral direction of the stent that face in the first direction and each of the first and second, turning points engages with exactly one connecting bar wherein the exactly one connecting bars engaging the first and second turning points connect to different turning points of the second annular support portion and between which a third turning point is located, the third turning point facing in the second direction and the third turning point engages two connecting bars of an annular support portion in adjacent relationship in the second direction with the first annular support portion with bar elements that extend in a meander configuration in the peripheral direction of the stent.

2. The stent of claim 1, wherein
   exactly two adjacent connecting bars engage in the region of the turning point which faces in the second direction.
3. The stent of claim 2, wherein
   the bar elements of the first and second annular support portions extend substantially in phase with each other with respect to the peripheral direction of the stent.
4. The stent of claim 1, wherein
   the bar elements of the first and second annular support portions extend substantially in phase with each other with respect to the peripheral direction of the stent.
5. The stent of claim 1, wherein
   the bar elements are adapted to increase the flexibility of the stent.
6. The stent of claim 5, wherein
   the connecting bars are adapted to increase the flexibility of the stent.
7. The stent of claim 6, wherein
   at least one annular support portion is formed by a bar element whose direction of curvature changes in a central region thereof between the turning points.
8. The stent of claim 7, wherein
   at least the connecting bars between the first and second annular support portions are of a curved configuration, wherein the direction of curvature changes in a central region between the two engagement points on the support portions.
9. The stent of claim 8, wherein
   the bar elements are adapted to produce a stress distribution which is as uniform as possible upon deformation and in particular expansion of the stent.
10. The stent of claim 9, wherein the connecting bars are adapted to produce a stress distribution which is as uniform as possible upon deformation and in particular expansion of the stent.
11. The stent of claim 10, wherein
    at least one annular support portion is formed by a bar element whose width decreases towards the center between two turning points.
12. The stent of claim 11, wherein
    the width at least of the connecting bars between the first and second support portions decreases towards the center between the two engagement points on the annular support portions.
13. The stent of claim 1, wherein
    the connecting bars are adapted to increase the flexibility of the stent.
14. The stent of claim 13, wherein
    at least one annular support portion is formed by a bar element whose direction of curvature changes in a central region thereof between the turning points.
15. The stent of claim 14, wherein
    at least the connecting bars between the first and second annular support portions are of a curved configuration, wherein the direction of curvature changes in a central region between the two engagement points on the support portions.
16. The stent of claim 15, wherein
    the bar elements are adapted to produce a stress distribution which is as uniform as possible upon deformation and in particular expansion of the stent.
17. The stent of claim 16, wherein
    the connecting bars are adapted to produce a stress distribution which is as uniform as possible upon deformation and in particular expansion of the stent.

18. The stent of claim 17, wherein
at least one annular support portion is formed by a bar element whose width decreases towards the center between two turning points.

19. The stent of claim 18, wherein
the width at least of the connecting bars between the first and second support portions decreases towards the center between the two engagement points on the annular support portions.

20. The stent of claim 1, wherein
at least one annular support portion is formed by a bar element whose direction of curvature changes in a central region thereof between the turning points.

21. The stent of claim 20, wherein
at least the connecting bars between the first and second annular support portions are of a curved configuration, wherein the direction of curvature changes in a central region between the two engagement points on the support portions.

22. The stent of claim 21, wherein
the bar elements are adapted to produce a stress distribution which is as uniform as possible upon deformation and in particular expansion of the stent.

23. The stent of claim wherein
the connecting bars are adapted to produce a stress distribution which is as uniform as possible upon deformation and in particular expansion of the stent.

24. The stent of claim 23, wherein
at least one annular support portion is formed by a bar element whose width decreases towards the center between two turning points.

25. The stent of claim 24, wherein
the width at least of the connecting bars between the first and second support portions decreases towards the center between the two engagement points on the annular support portions.

26. The stent of claim 1, wherein
at least the connecting bars between the first and second annular support portions are of a curved configuration, wherein the direction of curvature changes in a central region between the two engagement points on the support portions.

27. The stent of claim 26, wherein
the bar elements are adapted to produce a stress distribution which is as uniform as possible upon deformation and in particular expansion of the stent.

28. The stent of claim 27, wherein
the connecting bars are adapted to produce a stress distribution which is as uniform as possible upon deformation and in particular expansion of the stent.

29. The stent of claim 28, wherein
at last one annular support portion is formed by a bar element whose width decreases towards the center between two turning points.

30. The stent of claim 29, wherein
the width at least of the connecting bars between the first and second support portions decreases towards the center between the two engagement points on the annular support portions.

31. The stent of claim 1, wherein
the bar elements are adapted to produce a stress distribution which is as uniform as possible upon deformation and in particular expansion of the stent.

32. The stent of claim 31, wherein
the connecting bars are adapted to produce a stress distribution which is as uniform as possible upon deformation and in particular expansion of the stent.

33. The stent of claim 1, wherein
the connecting bars are adapted to produce a stress distribution which is as uniform as possible upon deformation and in particular expansion of the stent.

34. The stent of claim 33, wherein
at least one annular support portion is formed by a bar element whose width decreases towards the center between two turning points.

35. The stent of claim 34, wherein
the width at least of the connecting bars between the first and second support portions decreases towards the center between the two engagement points on the annular support portions.

36. The stent of claim 1, wherein
at least one annular support portion is formed by a bar element whose width decreases towards the center between two turning points.

37. The stent of claim 36, wherein
the width at least of the connecting bars between the first and second support portions decreases towards the center between the two engagement points on the annular support portions.

38. The stent of claim 1, wherein
the width at least of the connecting bars between the first and second support portions decreases towards the center between the two engagement points on the annular support portions.

39. The stent of claim 1, wherein
at least one annular support portion is formed by a bar element comprising bar element portions, the bar element extending in a meander configuration in the peripheral direction of the stent,
wherein each two bar element portions that are in adjacent relationship in the peripheral direction of the stent and that extend between the turning points form the limbs of a V-shape.

40. The stent of claim 1, wherein
the configuration of the bar elements and/or the connecting bars is selected in such a way that the stresses which occur therein upon expansion or the stent are above the elastic deformation limit and below the rupture limit of the stent material.

41. The stent of claim 1, wherein
the width of the bar elements and/or the connecting bars varies over the length thereof, in such a way that the stresses which occur therein upon expansion of the stent are above the elastic deformation limit and below the rupture limit of the stent material.

42. A catheter for stent implantation comprising a stent as set forth in claim 1.

* * * * *